United States Patent
Becker et al.

(10) Patent No.: US 10,968,421 B2
(45) Date of Patent: Apr. 6, 2021

(54) METHOD FOR MEASURING A PLURALITY OF PARAMETERS OF STATE OF A FLUID CONTAINED IN A CONTAINER

(71) Applicant: Sartorius Stedim Biotech GmbH, Goettingen (DE)

(72) Inventors: Mario Becker, Goettingen (DE); Gerhard Greller, Goettingen (DE); Christian Grimm, Heilbad Heiligenstadt (DE); Thorsten Adams, Goettingen (DE); Lars Boettcher, Melsungen (DE); Henry Weichert, Westewitz (DE)

(73) Assignee: Sartorius Stedim Biotech GmbH

( * ) Notice: Subject to any disclaimer, the term of this patent is extended or adjusted under 35 U.S.C. 154(b) by 438 days.

(21) Appl. No.: 15/737,847

(22) PCT Filed: Apr. 27, 2016

(86) PCT No.: PCT/EP2016/000678
§ 371 (c)(1),
(2) Date: Dec. 19, 2017

(87) PCT Pub. No.: WO2017/005332
PCT Pub. Date: Jan. 12, 2017

(65) Prior Publication Data
US 2019/0002810 A1 Jan. 3, 2019

(30) Foreign Application Priority Data
Jul. 6, 2015 (DE) .................... 10 2015 110 894.1

(51) Int. Cl.
*C12M 1/00* (2006.01)
*B01L 3/00* (2006.01)
(Continued)

(52) U.S. Cl.
CPC ......... *C12M 23/14* (2013.01); *B01F 15/0085* (2013.01); *B01L 3/505* (2013.01);
(Continued)

(58) Field of Classification Search
CPC ...... C12M 23/14; C12M 23/26; C12M 41/34; C12M 41/48; B01F 15/0085; B01L 3/505; G01N 35/00584; G01N 35/00871
See application file for complete search history.

(56) References Cited

U.S. PATENT DOCUMENTS

| 2005/0247114 | A1* | 11/2005 | Kahn | ...................... | G01N 33/18 |
| | | | | | 73/53.01 |
| 2005/0272146 | A1 | 12/2005 | Hodge et al. | | |
| 2013/0143221 | A1* | 6/2013 | Beauchemin | ........ | G01N 27/416 |
| | | | | | 435/6.12 |

FOREIGN PATENT DOCUMENTS

| EP | 2 829 598 | 1/2015 |
| WO | 2005/111602 | 11/2005 |
| WO | 2013/052836 | 4/2013 |

OTHER PUBLICATIONS

International Search Report dated Jul. 14, 2017.
(Continued)

*Primary Examiner* — Robert J Eom
(74) *Attorney, Agent, or Firm* — Gerald E. Hespos; Michael J. Porco; Matthew T. Hespos

(57) ABSTRACT

A method is provided for measuring parameters of state of a fluid contained in a container (10, 10') that has a sensor carrier plate with plural sensors (S01-S10, S01'-S10'). Each sensor has a sensor head in operative contact with the interior of the container (10, 10') and in operative contact with an external control unit (12). The external control unit (12) receives measurement data generated by the sensor heads of active sensors via their communication link and processes the data. An activation data record (24, 24') is
(Continued)

assigned to each sensor (S01-S10, S01'-S10') and is recorded in a manner that is accessible for the external control unit (12). The external control unit (12) first accesses the activation data records (24, 24'), then classifies the sensors (S01-S10, S01'-S10') as activatable or nonactivatable sensors, and subsequently activates only those sensors classified as activatable sensors.

10 Claims, 1 Drawing Sheet

(51) Int. Cl.
    *C12M 1/36*     (2006.01)
    *B01F 15/00*     (2006.01)
    *C12M 1/34*     (2006.01)
    *G01N 35/00*     (2006.01)

(52) U.S. Cl.
    CPC ............ *C12M 23/26* (2013.01); *C12M 41/34* (2013.01); *C12M 41/48* (2013.01); *G01N 35/00584* (2013.01); *G01N 35/00871* (2013.01)

(56) References Cited

OTHER PUBLICATIONS

Translation of International Preliminary Report on Patentability and Written Opinion for International Application No. PCT/EP2016/000678 dated Apr. 27, 2016.

\* cited by examiner

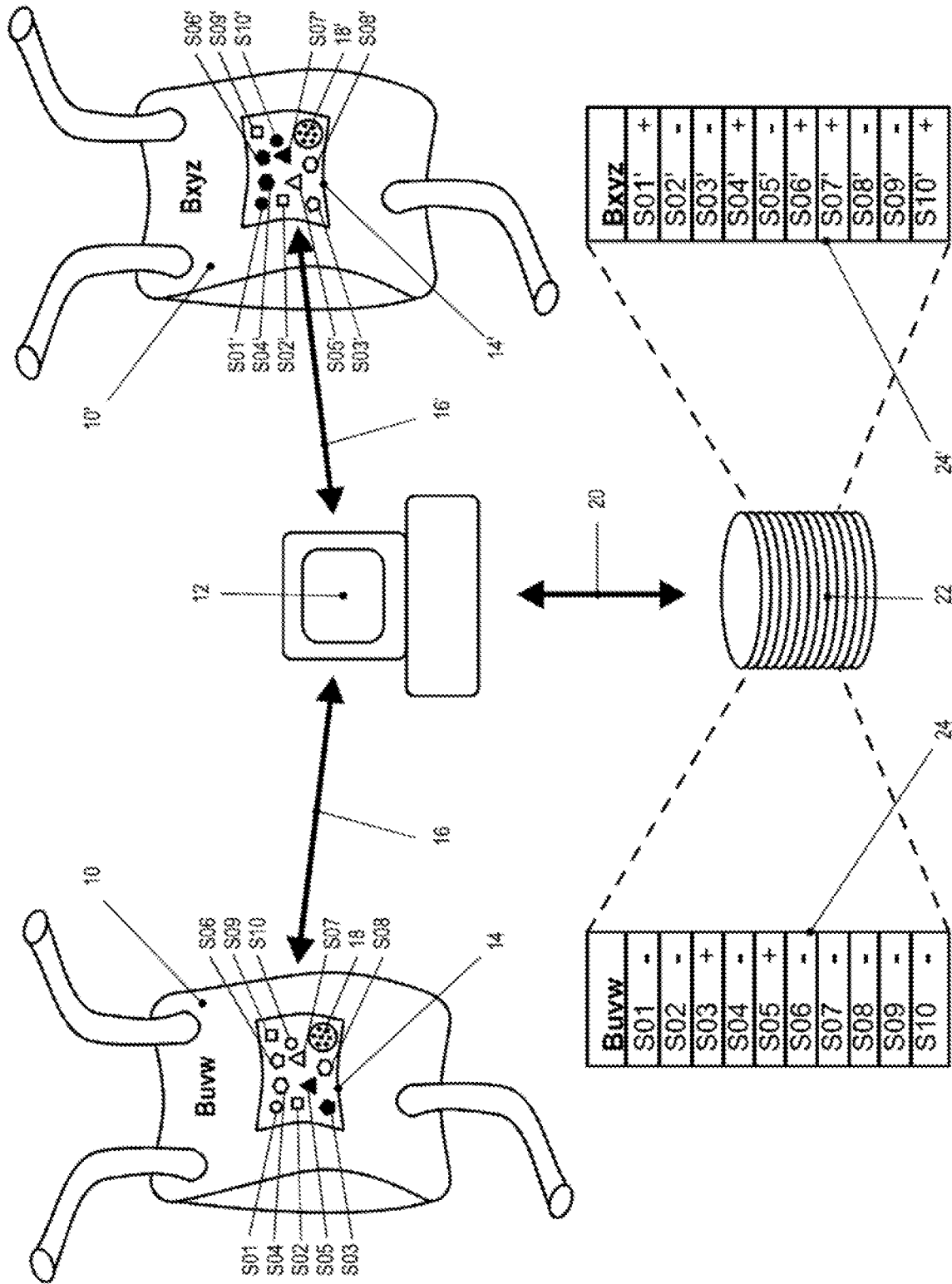

METHOD FOR MEASURING A PLURALITY OF PARAMETERS OF STATE OF A FLUID CONTAINED IN A CONTAINER

BACKGROUND

Field of the Invention

The invention relates to a method for measuring parameters of state of a fluid contained in a container. The container is configured for single use and a sensor carrier plate carrying sensors is secured in a fluid-tight manner on a wall of the container. Each sensor has a sensor head in active contact with the interior of the bioreactor and has a communication link connected to an external control unit in a data exchange connection. The external control unit receives and processes measurement data generated by the sensor heads of active sensors via their communication link.

Description of the Related Art

EP 2 829 598 A2 discloses a bioreactor in the form of a disposable bioreactor bag, i.e., a bag having flexible walls configured for a single use as a bioreactor. Such disposable bioreactor bags are being used increasingly in production processes in the biochemical and pharmaceutical industries. In comparison with the rigid and repeatedly reusable containers customary in the past, these disposable bags, which also are referred to as single-use bags, have substantial advantages with regard to hygiene and efficiency as well as the flexibility of work processes. However, the task of monitoring the reaction processes taking place in the interior of such bags is not without problems. Such monitoring always takes place by using suitable sensors, such as, electrochemical sensors, thermal sensors and conductivity sensors, optical and optochemical sensors, etc. For each specific reaction process in the interior of the bag, special sensors must be provided for monitoring the process. EP 2 829 598 A2 defines the generic type of single-use bioreactor bag and explains that single-use bioreactor bags may be provided with standardized ports in accordance with the technology that was also used previously in conjunction with rigid containers. Such ports provide an interface between the exterior of the bag and the interior of the bag, into which suitable sensors are inserted as needed. The sensor head then protrudes into the interior of the bag to establish contact with the fluid in the interior of the bag, as required for the specific measurement process. The part of the sensor located outside of the bag presents the interface to a communication link to an external control unit. This communication link may be designed to be an electrical cable or a fiberglass cable or may be designed to be wireless, for example, in the form of a radio link or an IR link. Such a communication link establishes a data exchange connection between sensors and the external control unit, so that data generated by the sensor head can be sent as analog or digital data over the communication link to the control unit and processed further there. EP 2 829 598 A2 discloses a so-called multiport as the mechanical interface, i.e., a plate having individual passages introduced into the wall of the bag in a physically bonded manner. Sensors required for the specific reaction process are inserted into the passages and activated as needed. However, the step of inserting a sensor into one of the ports is a critical step from the standpoint of hygiene, i.e., preserving the sterility of the interior of the bag. This can lead to the risk of contaminants penetrating into the interior of the bag and resulting in contamination of the fluid there unless the proper procedures are followed.

Inexpensive sensors have been developed and are suitable for a single use. Thus, it has become possible to equip the single-use containers at the manufacturing end with single-use sensors. These single-use containers are available as bags with flexible walls or as so-called "carboy" containers made of plastic with rigid walls. These single use sensors are arranged undetachably on a sensor carrier plate attached to the wall in a fluid-tight manner—for example, by physically bonded connection, for example, adhesive bonding or welding or also through a suitable force-locking or form-fitting connection. The manufacturing, i.e., equipping each individual bag with an individual assembly of different sensors, then takes place under hygienically optimized conditions on the part of the bag manufacturer and specifically in accordance with the customer's wishes. Corresponding single-use bioreactor bags are known from EP 2 503 320 B1, for example. However, this procedure, which is not objectionable from the standpoint of hygiene, does pose economic problems because individual manufacturing prevents inexpensive mass production.

The object of the present invention is to make available a method that will permit inexpensive mass production of single-use containers equipped with single-use sensors. The containers have a wall that is flexible in at least some areas or is rigid in at least some areas, for example, single-use bioreactor bags or single-use mixing containers.

SUMMARY

The invention relates to a method for measuring parameters of state of a fluid contained in a container. The container is a single use container. A sensor carrier plate is secured in a fluid-tight manner on a wall of the container and carries sensors. Each sensor has a sensor head in active contact with the interior of the bioreactor and has a communication link connected to an external control unit in a data exchange connection. The external control unit receives and processes measurement data generated by the sensor heads of active sensors via their communication link. An activation data record is assigned to each sensor and is stored in such a manner that it is accessible for the external control unit. The external control unit first accesses the activation data records that classify the sensors as activatable or nonactivatable sensors according to predetermined rules based on their respective assigned activation data record and thereinafter only the sensors classified as activatable are activated.

This method makes it possible to conform to the interests of manufacturers in a uniform mass production as well as the interests of customers in individual fabrication and a price that is linked to the possible uses. At the manufacturing end, this offers the possibility of equipping each container with walls that are flexible or rigid in at least some areas, for example, a bag with a battery of sensors that are all appropriate in the respective technical context so that the individual container, although more expensive with regard to its sensor equipment, this can be overcompensated by the cost of uniform mass production. On the other hand, the customer receives a container that has only the sensor functionality specifically needed (and paid for) by the customer. Individual fabrication is therefore no longer used on the part of the sensor hardware but instead only for the activation software, i.e., the individual use involves only the embodiment of the activation data records.

This therefore offers interesting price structure options in the manner of a license and authorization management for both customers and manufacturers. Thus, for example, a first user who needs only one or a few sensors for his specific bioreaction process or mixing process may need the same container, e.g., a bag with identical sensor equipment, as a second user, who needs a very extensive sensor system for his bioreaction process or mixing process. In addition, however, the first user will purchase only one or a few sensor activation licenses for his container, for example, his bag, and will pay a lower price accordingly than the second user, who must purchase a plurality of sensor activation licenses.

The activation data records for the individual sensors may be made accessible for the external control unit in various ways. For example, it is thus possible to provide each container with an individual data medium that can be read out by the external control unit. Alternatively, it is also possible to provide the users with the activation data records by some other route and to have them stored directly in the external control unit. It is of special interest, however, for the activation data records to be stored centrally in a server—in particular a server operated by the manufacturer—to which the users can have access for a network, for example, the Internet. Regardless of the specific type of availability of the activation data records, it is necessary, as recognized by those skilled in the art, to design the bags and/or sensors to be individually recognizable, but this can be accomplished in any known manner and in a variety of embodiments. The use of transponders, RFID chips, barcodes, QR codes, etc., can be mentioned purely as an example.

The specific technical implementation of the activation of individual sensors may take place in various ways, which do not ultimately depend on the respective sensors. Thus, in a first specific embodiment of the invention, it can be provided that at least one unactivated sensor detects no measurement data. This may occur, for example, due to the fact that the corresponding sensor does not receive the power required for its operation, for example, electric power supply, from the external control unit. In the case of optical sensors, for example, it is possible to provide that the corresponding sensor does not receive measured light from an external light source.

In many cases, however, the sensor carrier plate is provided with a central power supply and/or measurement light supply, so that even unactivated sensors are capable of working. In particular, but not only in these cases, it may be advantageous for at least one unactivated sensor to detect measurement data and for the external control unit not to receive these measurement data. This means that the unactivated sensors are in fact working, but they are not transmitting the measurement data generated by them to the external control unit. In other words, the nonactivation in this case relates to the communication link between the sensor and the external control unit.

However, there are also conceivable cases in which this type of activation and/or nonactivation is also not functional. One possible example relates to an essentially passive optical sensor with a glass fiber coupling to the external control unit. If such a sensor receives measurement light, e.g., from a central measurement light source, it will necessarily supply output light via its glass fiber communication link and will thus supply measurement data to the external control unit, but not only in these cases it may be more favorable if the external control unit receives measurement data from at least one unactivated sensor but does not process this data. The activation and/or nonactivation of the sensor thus take(s) place here in the external control unit. All of the aforementioned activation strategies and/or nonactivation strategies have in common the fact that the user does not receive any data made available by the unactivated sensors.

The container may be designed as a single-use mixing container or a single-use bioreactor, each having a flexible wall in at least some areas.

The single-use bioreactor may be a bag.

The container may be designed as a single-use mixing container or a single-use bioreactor, each having a rigid wall in at least some areas, also known by the term "carboy" in the prior art.

All the aforementioned containers have in common the fact that they can be manufactured from plastic in a particularly inexpensive manner.

As already explained, the communication link of a sensor may also be designed as a radio link, an electrically conductive cable, a glass fiber cable or in some other way. In the case of the cable coupling of multiple sensors, it is especially advantageous if multiple communication links, designed as electrically conductive cables, and/or multiple communication links, designed as optical glass fiber cables are bundled in standardized common cable. This corresponds to a refinement of the idea of undifferentiated mass production that is expanded here to also include a cable connection between a standardized sensor field and the external sensor unit. In this way regardless of the specific activation licensing, i.e., regardless of the actual functionality of the single-use container, the same reusable cable may always be used for its coupling.

Additional features and advantages of the invention are derived from the following specific description and the drawing.

BRIEF DESCRIPTION OF THE DRAWINGS

FIG. 1 shows a schematic diagram of the method according to the invention.

DETAILED DESCRIPTION

FIG. 1 shows the basic functioning of the method according to the invention in a schematic diagram. The FIGURE illustrates two identical containers with a flexible wall, for example, a single-use bioreactor bag or single-use mixing container 10, 10'. The container 10 shown at the left of FIG. 1 has the individual identifier symbolized as "Buvw" while the container 10' illustrated at the right of FIG. 1 has the individual identifier symbolized as "Bxyz." This identifier may be implemented in plain characters, as a barcode, as a QR code, as a transponder, as an RFID chip or in some other similar way. It is essential that the identifier can be read by an external control unit 12 so that the container 10, 10' can be recognized individually. Those skilled in the art will understand that in the context of the present invention it is not the individual identifier of the container, as such, that is important, but instead it is the identifiers of the sensors that are described below and are permanently attached to the wall of the bag 10, 10' during the manufacturing process.

Both containers 10, 10' have a sensor field 14, 14' of identical design, comprising a carrier plate attached to the wall of the respective container 10, 10' in a fluid-tight connection, as well as sensors S01-S10 and/or S01'-S10' permanently connected to the carrier plate. The sensors S01-S10, S01'-S10' have a data transmission connection to the external control unit 12, as indicated by communication arrows 16, 16'. This data transmission connection may be provided individually from each sensor S01-S10, S01'-S10' to the external control unit 12 or via an interface 18, 18' that includes a plurality of sensor inputs/outputs. Combinations are of course also possible so that, for example, some of the sensors S01-S10, S01'-S10' are connected to the external control unit in a hard-wired connection via glass fibers or electrical conductors while other ones of the sensors S01-S10, S01'-S10' have a wireless connection to the external control unit 12.

Furthermore, the sensors S01-S10, S01'-S10' together with their sensor heads (which are not shown separately) are in contact with the interior of the respective container 10, 10', so that the parameters of state of a fluid contained in the container 10, 10' can be measured by means of the sensors.

Despite the identical design of the containers 10, 10' and their sensor fields 14, 14' with regard to the hardware, they differ substantially in the specific embodiment in their functionality. In other words, as indicated by the communication arrow 20, the external control unit 12 has access to a databank 22, in which activation data records 24, 24' for the sensors S01-S10, S01'-S10' are saved individually for each bag. In the specific embodiment illustrated here, the sensors S03 and S05 are recorded as being activatable for the container Buvw (10), which is designed as a bag, for example, whereas the other sensors S01, S02, S04 and S06-S10 are recorded as being nonactivatable. FIG. 1 shows this as "+" and/or "−" symbols in the activation data record 24 as well as by solid or empty representation of the sensors in the sensor field 14. For the container Bxyz 10', however, which is designed as a bag, for example, the sensors S01', S04', S06', S07' and S10' are recorded as being activatable, whereas the sensors S02', 03', S05', S08' and S09' are recorded as being nonactivatable. They are represented in the activation data records 24' and in the sensor field 14' accordingly.

To carry out measurements with the sensor fields 14, 14', the external control unit first accesses the activation data records 24, 24' and then accesses only those sensors that are recorded as being activatable for each container 10, 10'. The user does not receive any measurement data from the other sensors that are not recorded as being activatable. It does not matter where the sensor blockade occurs. As already discussed in the general part of the description, this may take place at the level of the sensor head, at the level of the communication link to the external control unit or in the external control unit itself.

Those skilled in the art will understand that this procedure allows a broad spectrum of license management strategies. Whereas the manufacturer enjoys the advantage of having to manufacture only one type of identical container without any individual fabrication on the hardware end, the user enjoys the advantage of having to pay debitable and creditable licenses only for those functionalities which he actually needs for his individual process. The cost advantages achieved by means of identical mass production in contrast with individual fabrication result in savings at the manufacturing end as well as at the user's end, in particular when the containers are designed as single-use mixing containers or single-use bioreactors.

The specific embodiments illustrated in the figures and discussed in the specific description are of course only illustrative examples of embodiments of the present invention. Those skilled in the art are thus provided with a broad spectrum of possible variations in light of the present disclosure.

LIST OF REFERENCE NUMERALS 10, 10' Container
12 External control unit
14, 14' Sensor field
16, 16' Communication arrow
18, 18' Standardized interface
20 Communication arrow
22 Databank
24, 24' Activation data records
S01, S01' Sensor
S02, S02' Sensor
S03, S03' Sensor
S04, S04' Sensor
S05, S05' Sensor
S06, S06' Sensor
S07, S07' Sensor
S08, S08' Sensor
S09, S09' Sensor
S10, S10' Sensor

The invention claimed is:

1. A method for measuring a plurality of parameters of state of a fluid contained in a container (10, 10') configured for a single use, wherein a sensor carrier plate is secured on a wall of the container (10, 10') in a fluid-tight manner, the carrier plate having a plurality of sensors (S01-S10, S01'-S10') that measure parameters of state of the fluid, each of which has a sensor head in active contact with an interior of the container (10, 10') and has a communication link with a data exchange connection to an external control unit (12), and wherein the external control unit (12) receives measurement data generated by sensor heads of active sensors (S03, S05, S01', S04', S06', S07', S10') via their communication link and processes them, the method comprising:
  associating an activation data record (24, 24') with each of the sensors (S01-S10, S01'-S10'), the activation data records (24, 24') classifying each of the sensors (S01-S10, S01'-S10') as being either activatable or nonactivatable;
  storing the activation data record (24, 24') in a storage that is accessible for the external control unit (12);
  using the external control unit (12) to access the activation data records (24, 24') in the storage;
  classifying the sensors (S01-S10, S01'-S10') as being activatable or nonactivatable according to predetermined rules, based on the respective associated activation data records (24, 24'); and
  subsequently activating the sensors (S03, S05, S01', S04', S06', S07', S10') classified as activatable sensors.

2. The method of claim 1, wherein at least one nonactivatable sensor (S01, S02, S04, S06-S10; S02', S03', S05', S08', S09') does not detect measurement data.

3. The method of claim 1, wherein at least one nonactivatable sensors (S01, S02, S04, S06-S10; S02', S03', S05', S08', S09') detects measurement data and the external control unit (12) does not receive the measurement data from the at least one nonactivated sensors (S01, S02, S04, S06-S10; S02', S03', S05', S08', S09').

4. The method of claim 1, wherein the external control unit (12) receives measurement data from at least one nonactivatable sensor (S01, S02, S04, S06-S10; S02', S03', S05', S08', S09') and does not process the data.

5. The method of claim 1, wherein the communication link of at least one sensor (S01-S10, S01'-S10') is a radio link.

6. The method of claim 1, wherein the communication link of at least one sensor (S01-S10, S01'-S10') is an electrically conductive cable.

7. The method of claim 1, wherein the communication link of at least one sensor (S01-S10, S01'-S10') is an optical glass fiber cable.

8. The method of claim 7, wherein plural of the communication links are optical glass fiber cables bundled in a standardized common cable.

9. The method of claim 1, wherein the container (10, 10') is a single-use mixing container or a single-use bioreactor having a flexible or rigid wall in at least some areas.

10. The method according to claim 6, wherein plural of the communication links are electrically-conductive cables bundled in a standardized common cable.

* * * * *